United States Patent
Squirrell et al.

(10) Patent No.: US 7,652,266 B2
(45) Date of Patent: Jan. 26, 2010

(54) FLUORESCENCE-BASED DETECTION METHODS AND APPARATUS

(75) Inventors: David James Squirrell, Wiltshire (GB); Martin Alan Lee, Wiltshire (GB)

(73) Assignee: Engima Diagnostics Limited (GB)

( * ) Notice: Subject to any disclaimer, the term of this patent is extended or adjusted under 35 U.S.C. 154(b) by 0 days.

(21) Appl. No.: 12/095,444

(22) PCT Filed: Dec. 11, 2006

(86) PCT No.: PCT/GB2006/004592

§ 371 (c)(1), (2), (4) Date: Jul. 25, 2008

(87) PCT Pub. No.: WO2007/066126

PCT Pub. Date: Jun. 14, 2007

(65) Prior Publication Data
US 2008/0290292 A1    Nov. 27, 2008

(30) Foreign Application Priority Data
Dec. 9, 2005    (GB) ................................ 0525072.5

(51) Int. Cl.
*F21V 9/16* (2006.01)
(52) U.S. Cl. ................................. 250/458.1
(58) Field of Classification Search ............. 250/458.1, 250/459.1, 461.1, 461.2
See application file for complete search history.

(56) References Cited

U.S. PATENT DOCUMENTS

| | | | |
|---|---|---|---|
| 3,971,951 A | | 7/1976 | Rikukawa et al. |
| 5,294,799 A | | 3/1994 | Aslund et al. |
| 5,814,820 A | * | 9/1998 | Dong et al. ............... 250/458.1 |
| 6,184,535 B1 | * | 2/2001 | Kashima et al. .......... 250/459.1 |
| 2002/0158212 A1 | * | 10/2002 | French et al. ............ 250/459.1 |
| 2003/0092982 A1 | * | 5/2003 | Eppstein .................. 600/411 |
| 2004/0131687 A1 | * | 7/2004 | Kraft et al. ............... 424/486 |
| 2005/0009101 A1 | * | 1/2005 | Blackburn ................ 435/7.1 |

(Continued)

FOREIGN PATENT DOCUMENTS

DE    3604815 A1    8/1987

OTHER PUBLICATIONS

Schneckkenburger et al., "Time-resolved in situ measurement of mitochondrial malfunction by energy transfer spectroscopy," Oct. 2000, Journal of Biomedical Optics, vol. 5, No. 4, pp. 362-366.*

(Continued)

*Primary Examiner*—David P Porta
*Assistant Examiner*—Kiho Kim (57) ABSTRACT

In apparatus for detecting the emission of fluorescent radiation from a sample in response to excitation by two or more different radiation sources (145, 160) over the same time period, each radiation source (145, 160) is imprinted with a modulation regime which can then be separately detected in the emitted fluorescent radiation. For instance in techniques based on fluorescent resonant energy transfer ("FRET"), the drive current to two or more different LED sources (145, 160) may be frequency modulated, or pulse width modulated, according to different modulation regimes. Responses of the sample, for instance of different donor/acceptor probes contained in the sample, to each of the sources (145, 160) can then be separately detected by means of the different modulation regimes, even where the wavelengths or wavelength ranges of the responses are the same or overlapping.

29 Claims, 5 Drawing Sheets

U.S. PATENT DOCUMENTS

2005/0272088 A1* 12/2005 Cook et al. .................... 435/6
2007/0096038 A1* 5/2007 Tsai et al. ................ 250/458.1

OTHER PUBLICATIONS

Wokosin et al., "Pulse width considerations for multi-photon excitation laser scanning fluorescence imaging,", 1998, Proceedings of SPIE, vol. 3260, pp. 115-122.*

Katz et al., "Ultraviolet and blue 2D fluorescence mapping of gynecological tissues," 2000, Proceedings of SPIE, vol. 3917, pp. 200-203.*

Sytsma et al., "The development of a confocal laser scanning fluorescence microscope using two-photon excitation in combination with time-gated detection," 1995, Proceedings of SPIE, vol. 2412, pp. 110-114.*

International Search Report for PCT/GB2006/004592 dated Feb. 21, 2007; 2 pages.

* cited by examiner

| Fluorescein Concentration | Response |
|---|---|
| 0 | 30 |
| 0.1 pM | 50 |
| 1 pM | 50 |
| 10 pM | 150 |
| 100 pM | 200 |
| 1 nM | 800 |
| 10 nM | 5,000 |
| 100 nM | 14,000 |

FIGURE 8

FLUORESCENCE-BASED DETECTION METHODS AND APPARATUS

The present invention relates to fluorescence-based detection methods and apparatus such as might be used in assays or imaging. It finds particular application in methods and apparatus for fluorescence microscopy and methods and apparatus based on fluorescent resonant energy transfer.

In luminescence-based assay or imaging methods, susceptible molecules are excited by a stimulus, physical, chemical or mechanical, and subsequently emit light which can be detected. The emitted light can be used to find the position of the molecules and can thus be used in imaging, and/or to detect an involvement of the emitting molecule in a process.

A convenient form of stimulus is light which can be directed onto a sample containing the susceptible molecules and this form of luminescence is known as fluorescence. The emitted light has a different wavelength or wavelength range from that of the stimulating light so that it can be relatively easily detected in the presence of the stimulating light. Neither the stimulating light nor the emitted light is necessarily in the visible spectrum although clearly there needs to be a suitable method of detecting the emitted light.

In fluorescent resonant energy transfer ("FRET") assay techniques, the progress of a process in a sample can be determined from the emitted light. Susceptible moieties are present in two types, these types consisting of a donor moiety and an acceptor moiety. The moieties can take various forms such as separate fluorescent molecules or different fluorophore groups on the same molecule, or might not have a molecular form but be for instance particulate such as fluorescent beads or fluorescent quantum dots. On their own, donors fluoresce in response to stimulating light (also referred to herein as "excitation radiation") delivered to the sample. However, if an acceptor is physically close by, there is a transfer of excitation energy between dipoles which will quench the donor's fluorescence and may instead lead to fluorescence by the acceptor. This is sometimes known as the "Förster" resonance energy transfer. The extent of energy transfer depends on the separation distance between the donor and acceptor. The FRET assay techniques depend on the effect of a process on the physical proximity of donor/acceptor pairs. When they are sufficiently close together, there is transfer of energy from the donor to the acceptor and the overall fluorescent output of the pair is affected by that. When the pair is separated, the transfer of energy is reduced or stopped and the overall fluorescent output of the pair is detectably different. Thus a process which changes the physical proximity of donor/acceptor pairs in a sample causes a detectable change in the spectral content of light emitted by the sample, giving a measure of the progress of the process.

Susceptible fluorophores, including donor/acceptor pairs, are sometimes built into structures known as "probes". A probe has the character that it will behave in a certain way in a sample so that fluorescence emitted from the probe location will give useful information. For example, the probe might take up certain sites in which case the fluorescence will show those sites. In FRET, the probe is often chosen so that it will be either constructed or divided by the process under assay, the donor and the acceptor being located on different parts of the probe so that they are brought together or separated as the probe is constructed or divided. Probes may alternatively have more than one component, these components carrying a donor and an acceptor respectively and being either brought close together or separated by the process under assay.

The materials providing donor and acceptor fluorophores are often referred to as dyes and well known examples of such dyes include fluorescein (blue excitation, green emission: usually used as a donor) and rhodamine (green excitation, red emission: usually used as an acceptor).

The change in physical proximity of a donor/acceptor pair can be detected in different ways. The acceptor may itself fluoresce when it receives energy from the donor, but at a different wavelength from that at which the donor fluoresces. Thus the change in physical proximity can be detected by measuring a change in the level of fluorescent output at the wavelength of either donor or acceptor. Whichever is monitored in order to detect that change is referred to as a "reporter", whether it is the donor or the acceptor. Some acceptors do not themselves fluoresce but merely "quench" the fluorescence of the donor. These are known as "dark quenchers" and the donor in this case is necessarily the reporter. Monitoring or detecting arrangements incorporating a reporter can be generally referred to as reporter systems.

Acceptor molecules are also sometimes known as "receptors" but, depending on the process being monitored, there can be confusion with other elements of the process and the term acceptor is generally used herein.

Processes which can be monitored using FRET techniques include protein-protein interactions, nucleic acid-nucleic acid interactions and protein-nucleic acid interactions. For example, in the binding of epidermal growth factor ("EGF") to receptors in a cell membrane, whereupon the receptors dimerize, individual units of EGF are labelled beforehand, some with a donor molecule and some with an acceptor molecule. The dimerization of the receptors in the membrane brings at least some donor/acceptor molecule pairs close together, bringing about a detectable change in spectral content of light emitted by the sample as described above. Immunoassays may be constructed on similar principles such as by using two fluorophore-labelled antibodies to form a FRET pair through simultaneous binding to an antigen to form an antibody-antigen-antibody sandwich complex, or bringing a fluorophore-labelled antibody into the proximity of a fluorescent bead in the presence of antigen through the agency of a capture antibody immobilised at the surface of the bead. In terms of nucleic acid interactions, FRET labelled reagents may be used in "fluorescence in situ hybridisation" (FISH) for the staining of cells and tissues, in nucleic acid hybridisation assays (particularly in array formats in "DNA chips"), and in detecting the operation of a DNA replicating enzyme where a sequence-specific probe containing a donor/acceptor pair may be added to the reagent master mix. As the enzyme moves along the DNA, it meets the probe and cleaves it, thus separating the donor/acceptor pair, again bringing about a change in spectral content of light emitted, as described above.

A very successful example of a known process in which an enzyme replicates DNA is the polymerase chain reaction ("PCR") in which the double helix of sample DNA is denatured into its two strands of nucleotides and then each strand is copied by the action of a polymerase to create two new double helixes. The process is repeated using a number of heating and cooling cycles to get a large increase in the quantity of sample DNA. The copying process is triggered by the binding of a "primer" to each strand to be used as a template. A primer is a single chain of nucleotides in a specific order that can bind to a complementary sequence of nucleotides in a denatured strand of DNA. Starting from the primer, the polymerase can then "read" the template strand and match it with complementary nucleotides very quickly. The result is two new helixes in place of the first, each composed of one of the original strands plus its newly assembled complementary strand.

To monitor a PCR process, one or more probes are also bound to the denatured strand of DNA. A probe follows the same principle as a primer but does not trigger copying. Instead, it carries a donor, an acceptor or both and binds to one or more positions along the strand. If it is then hydrolysed by the polymerase as it works its way along the strand from the primer, with consequent separating of a donor/acceptor pair, measurable changes to FRET may be detected.

Other probes using a donor/acceptor pair and thus useful in FRET-based assays include probes using dual hybridisation in which the donor and acceptor are carried on different structures which are brought physically close together by binding to adjacent positions along a strand if a target code is present in the strand, "molecular beacons" in which the donor and acceptor are carried at respective ends of a looped structure which unloops to bind to a strand thereby separating the donor/acceptor pair, and "Resonsense" where the donor/acceptor pair are a labelled probe and an intercalating dye.

PCR processes and FRET assay techniques are discussed in "Real-Time PCR: An Essential Guide" edited by Edwards, Logan and Saunders, published in 2004 by Horizon Bioscience, ISBN 0-9545232-7-X. As will be seen there, it is known to multiplex measurements on one sample. There may be more than one process that might occur in the sample and these may be separately detectable by using different probes, the probes in turn being "labelled" by carrying different donor/acceptor pair combinations. For example, donor/acceptor pairs can differ in using different donor molecules, fluorescing at different wavelength ranges, or in using different acceptor molecules. If there is more than one type of donor, it is known to use a "universal acceptor" technique in which one type of acceptor molecule accepts resonant energy from more than one type of donor. A universal acceptor technique simplifies detection since only one wavelength has to be detected, that of the acceptor fluorescence. Depending on the types of donor, it may be necessary to provide excitation radiation of more than one wavelength. Similarly, if there is more than one type of acceptor, it is known to use a "universal donor" technique in which the resonant energy of one donor can be accepted by more than one acceptor. Although each probe type may carry the same donor, the different probe types are distinguishable by the fluorescence wavelength range of the respective acceptors. Both the universal donor and the universal acceptor approaches can be extended by using more than one universal donor and/or acceptor so that groups of probes will share the same donor or acceptor.

In known arrangements using the universal acceptor format, responses from different probes cannot be directly distinguished from one another by measuring acceptor fluorescence since the acceptor molecule will fluoresce in the same way in response to each of the different donors. Measurements have thus been run in sequence, for example at a series of different excitation wavelengths. This does not allow for continuous monitoring of fluorescence changes in processes such as nucleic acid amplification reactions. Even if the fluorescent response of a sample to different excitation wavelengths can be directly distinguished, for instance because different donor molecules fluoresce at different wavelengths in a universal "quencher" format, or the universal donor format is used and different acceptor molecules fluoresce at different wavelengths, it can in practice be difficult to obtain a multiplex of very many different probes. For example, there is a practical limit of about four when using FRET in real-time to monitor the process of PCR. This is because fluorescence emissions tend to be relatively broad in wavelength range.

According to a first aspect of embodiments of the present invention, there is provided apparatus for detecting the emission of fluorescent radiation from a sample in response to excitation by a radiation source, the apparatus comprising:

i) a sample irradiator for irradiating the sample with excitation radiation from at least two sources over the same time period, the two sources providing excitation radiation of different wavelengths;

ii) a modulation arrangement for modulating the excitation radiation of each of said at least two sources according to a different respective modulation regime; and iii) an emission detector for detecting emission of fluorescent radiation from the sample, wherein the emission detector is adapted to detect each of said different respective modulation regimes in emitted radiation such that responses of the sample to said at least two sources can be separately detected.

Because it can deal with excitation radiation from at least two sources over the same time period, apparatus according to an embodiment of the invention is distinguished in that the sample irradiator is designed to deliver the excitation radiation from at least two sources to the sample over the same time period. For example, the sample irradiator might comprise at least one radiation deflector, such as a half mirror or dichroic mirror, for deflecting excitation radiation provided by at least one of said sources onto a path shared with excitation radiation provided by at least one other of said sources for delivery to the sample.

A distinctive feature of embodiments of the invention lies in the fact that the wavelengths of emissions from the sample in response to different sources can potentially be the same or overlapping. This is of course because different emissions can instead be distinguished by their modulation regimes. Thus the emission detector might comprise a single or shared filter for filtering emission of fluorescent radiation from the sample in response to different sources. The single or shared filter can help to reduce noise in the system but there is no necessity to provide two or more different filters, or indeed two or more different radiation paths, in order to separate the different responses.

In an embodiment of the present invention, it is possible to use at least two different excitation sources at the same time to irradiate a sample and still to distinguish the fluorescent response of the sample to excitation by just one of the sources, even where the wavelength of the fluorescent response would be the same for each source. This can be done by detecting the distinctive modulation regimes associated with each radiation source in the sample emissions. It is thus possible to detect, and if required to monitor the progress of, at least two different processes in the same sample, or two different aspects of one process, by using at least two different probes. This is possible even where there is only one wavelength or wavelength range in the sample emissions and thus wavelength has been lost as a way of distinguishing which excitation source a sample is responding to. Effectively, each distinctive modulation regime is being used to "label" or imprint a particular excitation source in a way that can be detected in fluorescence produced by a reporter in a sample, even when the wavelength or wavelength range is the same for fluorescence produced in response to each of the excitation sources.

Circumstances in which there might be only one wavelength or wavelength range in the sample emissions but at least two different excitation sources include the use of a universal acceptor with more than one different donor. In the case of the use of two different donors as reporters (that is, with a universal quencher) where the donors respond to different excitation sources but happen to fluoresce at the same or overlapping wavelengths, the imprinting of a modulation signal via the excitation sources may thus be used to increase the analytical separation of the emission signals.

Thus an embodiment of the invention in its first aspect might comprise apparatus for use in fluorescent resonant energy transfer assays for detecting the emission of fluorescent radiation from a sample, the sample containing at least two different probes, each probe comprising a donor/acceptor pair, wherein the wavelength of the excitation radiation of each of said at least two sources is selected to excite a response from a different respective probe in the sample, and the emission detector is adapted to detect each of said different respective modulation regimes in emitted radiation such that responses of the at least two different probes to said at least two sources can be separately detected.

A convenient form of modulation arrangement for use in embodiments of the invention is one which imposes periodic modulation of the amplitude or intensity of a radiation source to give a distinctive modulation regime. Where the radiation source is a light emitting diode, this might be done for example by a sinusoidal variation in the drive current to the diode. Alternatively, the modulation might be applied to emitted radiation of the source, for instance by inserting an opto-electronic modulator, an oscillating shutter or a rotating wheel with spaced apertures in the radiation path between the source and the sample. In this case, the excitation radiation emitted by the source might comprise a pulse train, the modulation arrangement being adapted to control one or more parameters of the pulse train to give the modulation regime for that source. Parameters of a pulse train that might be modulated in this way include pulse frequency or phase in the 0.1 kilohertz to 10 megahertz range and pulse width in the 0.1 microsecond to 10 millisecond range.

It is an option also to use more than one excitation wavelength, thus increasing the number of different responses given by a sample which can be detected. In this case, the emission detector might be adapted to detect emission of fluorescent radiation at first and second wavelengths (or wavelength ranges) independently, whereby at least four different responses of the sample can be separately detected, distinguished in each case by modulation regime and/or by wavelength. Using different modulation regimes allows the principle to be extended further, for instance to six or a greater number of different responses.

By allowing multiple excitation wavelengths to be used simultaneously, embodiments of the invention enhance the capacity for making kinetic measurements which are particularly useful in processes such as real-time PCR. Real-time PCR is a very dynamic system with non-specific thermal cycling-induced fluorescence changes occurring over timescales of tens of seconds. For example, there can be a complicated relationship between pH, temperature and the wavelength ranges of fluorescent emissions. Fluorescence reporting from a probe however used, operating for instance within a primer or in product strand annealing and melting, can take place in tenths of seconds to seconds. If fluorescence reporting can only be detected sequentially, there may not be time to capture the full richness of the fluorescence information available without having to repeat an assay—which can introduce error and takes more time and more sample material. Using embodiments of the present invention however, reporting from more than one, indeed several, probes can be detected at the same time.

In the past, it has been possible to distinguish up to four different fluorescent emissions, and this has in many cases been only with difficulty. Using an embodiment of the present invention to "label" each excitation source breaks down this practical barrier so that a far greater number of fluorescent emissions can be distinguished, allowing many more probes to be detected at the same time. Examples of assays where this might be important might be based on the known "triplex assay" in which sample DNA is put through PCR using a first probe, control DNA is put through PCR at the same time using a second probe, and a control probe is also used in order to authenticate the PCR process. In some assays, there may be multiple PCR processes to follow, as well as using control DNA and one or more control probes. Embodiments of the invention support the simultaneous monitoring of all these processes, five or more, in the same sample and at the same time.

Thus the introduction of source modulation in the monitoring of PCR processes has significant benefits, even though known excitation sources used in such detection and/or monitoring are already distinguished by wavelength. It has been recognised in making the present invention that the ability to distinguish the sources of excitation radiation by wavelength does not carry through to the domain of the probe emissions since two different probes might well respond to two different excitation sources by emitting similar or overlapping fluorescent wavelength ranges.

A further benefit of embodiments of the invention is improved sensitivity of fluorescence detection through improvement in signal to noise ratios.

As indicated above, embodiments of the invention might be used to detect and distinguish an emission for various purposes, such as making one or more measurements or for monitoring an emission over a period of time.

According to a second aspect of embodiments of the present invention, there is provided apparatus for detecting fluorescent radiation emitted from a sample during the course of a nucleic acid amplification reaction, in response to excitation by a radiation source, the apparatus comprising:

i) a sample irradiator for irradiating the sample with excitation radiation from a source;

ii) a modulation arrangement for modulating the excitation radiation according to a detectable modulation regime; and iii) an emission detector for detecting emission of fluorescent radiation from the sample, wherein the emission detector is adapted to detect said modulation regime in emitted radiation such that a response of the sample to the source can be detected in the presence of one or more other radiation inputs to the emission detector.

An embodiment of the invention in its second aspect might comprise apparatus wherein the sample irradiator is adapted to irradiate the sample with excitation radiation from at least two different sources and the emission detector is adapted to detect two or more different responses of the sample, each response being generated by a different probe of the reporter system, each probe comprising a donor/acceptor pair, in a process using fluorescent resonant energy transfer.

According to a third aspect of the invention, there is provided a method of detecting fluorescent emissions from a sample, the method comprising detecting at least two fluorescent emissions, the at least two emissions being differentiated by different respective modulation regimes.

In a method according to an embodiment of the invention in its third aspect, detection of each fluorescent emission can be done separately by detecting the modulation regime appropriate to each fluorescent emission.

Embodiments of the invention in its third aspect might be applied using apparatus according to embodiments of the invention in its first and second aspects. Any feature described in relation to one aspect or to any one embodiment of the invention may be applied in relation to one or more other aspects or embodiments of the invention if appropriate.

Embodiments of the invention might find application in non-biological methods and processes, since the only requirement of FRET techniques for example is that donor/acceptor pairs move in relation to one another in the course of a method or process. However, there are clearly many applications where the sample comprises a biological sample. One such application is processes based on nucleic acid amplification reaction, such as a real-time polymerase chain reaction. However, applications of embodiments of the invention extend beyond FRET-based assays and PCR processes. For example, differentiation of emissions by modulation may also be found useful in fluorescent-based imaging in which different components in a sample show their position by a fluorescent response to excitation radiation. Just as in FRET-based assays and PCR processes, it may be important to distinguish emissions by components which cannot easily be distinguished by emission wavelength but can be excited by different excitation sources. Again, distinctive modulation of the different sources can be detectable in the responses thereto. This may be particularly relevant in imaging applications where a typical detector such as a CCD camera lacks intrinsic wavelength discrimination and requires filter arrangements to achieve colour separation with consequent penalties in terms of sensitivity, simplicity and cost.

A fluorescent radiation probe monitor for use in PCR assays will now be described as an embodiment of the present invention, by way of example only, with reference to the accompanying figures in which.

Figure 1:
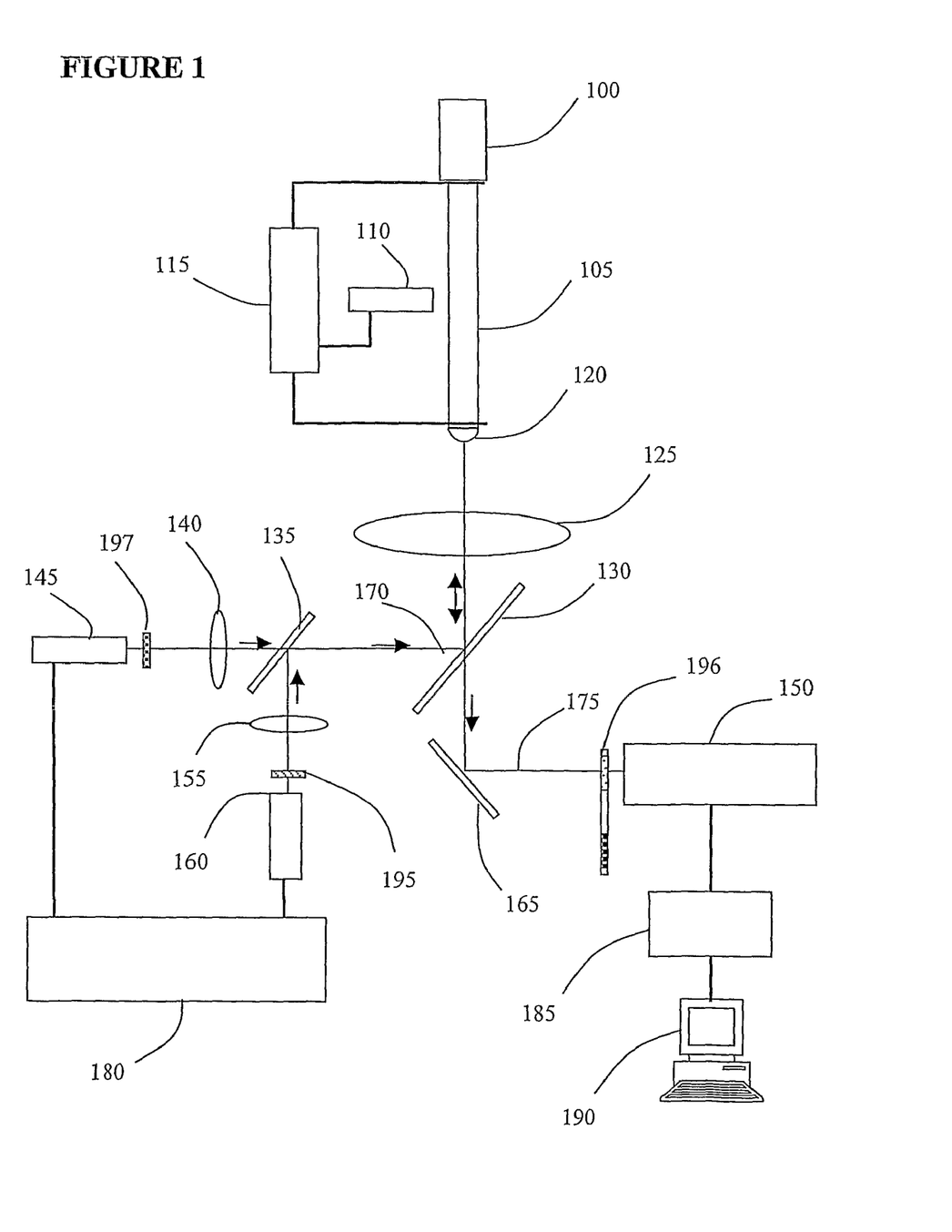
FIG. 1 shows a schematic plan view of the monitor.

Referring to FIG. 1, a sample for assay is delivered in known manner, via a sample delivery input 100, to a 15 mm glass capillary coated in an electrically conducting polymer to make a capillary assembly 105. The capillary assembly 105 is provided with a heating circuit 115 to deliver heat via the polymer and an infrared thermopile 110 for dynamic feedback control to the heating circuit 115. Excitation radiation 170 for use in monitoring fluorescent probe activity is delivered to the capillary assembly 105 from two sources 145, 160, via respective lenses 140, 155, a half mirror 135, a dichroic mirror 130 and a further lens 125. The capillary itself has a beaded end 120 through which it receives the excitation radiation 170 and delivers fluorescent output. Such arrangements are of known type. The dichroic mirror 130 is adapted to reflect radiation at the wavelengths of the excitation radiation, and thus delivers the excitation radiation via the further lens 125 to the capillary assembly 105, but to transmit radiation at the wavelengths of fluorescent probes present in the sample. Fluorescent radiation 175 emitted from the sample can thus be gathered by the further lens 125 and delivered along a different light path by the dichroic mirror 130 to a radiation detector 150.

Short pass filters 195, 197 are used at the output of each source 145, 160 to limit the excitation radiation 170 to desired wavelengths and to block parasitic excitation. A long pass filter 196 is used at the input to the detector 150 to reduce noise from sources other than the fluorescent probes present in the sample.

Figure 2:
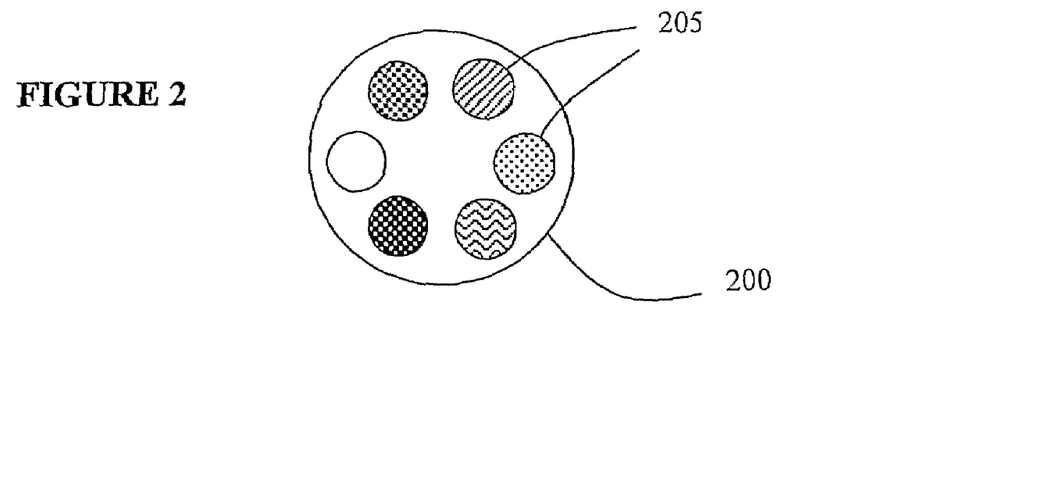
FIG. 2 shows a schematic front elevation of a filter used in the monitor of FIG. 1.

Referring to FIG. 2, each filter 195, 196, 197 is of known type and can optionally comprise a disc 200 with a number of different filtering apertures 205. The disc 200 can be rotated to present a selected filtering aperture 205 to a beam and can thus be used to filter any of a number of different wavelength ranges. In the arrangement shown in FIG. 1, only the long pass filter 196 comprises a disc 200, the short pass filters 195, 197 each comprising just a simple filter.

Referring again to FIG. 1, the two sources 145, 160 emit excitation radiation 170 at wavelengths centred on 360 nm (violet) and 480 nm (blue) respectively. Each source comprises a light emitting diode ("LED") which is driven to emit excitation radiation by delivery of a drive current. Variations in the drive current will vary the intensity of the delivered excitation radiation and each source 145, 160 is driven via a modulation arrangement 180 to show a sinusoidal-based variation in intensity. The frequency is specific to each source, producing a characteristic modulation regime for each source. For example, the violet source 145 might be modulated at 5 kHZ and the blue source 160 at 12 kHZ.

The frequencies mentioned above, 5 kHZ and 12 kHZ, are examples only. It would be possible to apply modulation anywhere in a wide range of frequency, for example from 65 Hz to 10 MHz. This range is suitable because it runs from significantly above US mains frequency (60 Hz) up to a frequency above which fluorescence relaxation times (around 100 nanoseconds) would become significant.

Suitable modulation arrangements 180 for the drive current of a photodiode which could be used are known and thus not described in detail here. One modulation arrangement 180 might in practice have more than one drive current output and thus control the drive current of more than one photodiode 145, 160. Such an arrangement 180 might incorporate control software for setting the respective drive currents supplied at each output to a photodiode 145, 160. Alternatively, the modulation arrangement 180 might in practice be represented by two or more separate modulating arrangements, each one independently controllable to set the respective drive currents.

Variation of the drive current to a photodiode can cause colour drift in the diode output but this is generally slight and may not be a problem. An alternative to intensity modulation of the drive current however is pulse width or repetition rate modulation which could be applied as an on/off switch to the drive current of the or each photodiode 145, 160 or to the respective output beams. Again, suitable modulation arrangements 180 are known and not described in detail herein. For example, the modulation arrangement 180 could supply control signal(s) to one or more opto-electronic modulators (not shown) for selectively blocking the output beam(s). Pulse-based modulation avoids colour drift but can introduce harmonics to the system which may need to be filtered out.

Fluorescent probes in the capillary assembly 105 fluoresce in known manner in response to the excitation radiation 170. Depending on the progress of processes occurring in the capillary assembly 105 and the specific probes in use, fluorescent radiation from one or more probes is emitted via the beaded end 120 of the capillary, picked up via the further lens 125 and delivered via the long pass filter 196 to the radiation detector 150. A suitable known form of detector 150 is a photodiode with associated amplifier, thus providing an amplified electrical output signal representative of the level of activity of one or more processes being monitored by the probe(s). This output signal is delivered to a signal analyser 185 and can be viewed on a monitor 190 and/or stored.

The output signal of the radiation detector 150 will reflect fluctuations in the fluorescent radiation being detected. Thus the characteristic modulation regime of a source, which will in turn produce modulation in the fluorescent radiation, is carried through to the electrical output of the detector 150. If there is more than one source 145, 160, there will be more than one characteristic modulation regime. If fluorescence is stimulated by each of the sources 145, 160 during the same time period and detected by the same detector, the modulation regimes will both be present in the electrical output signal of the detector 150.

Figure 3:
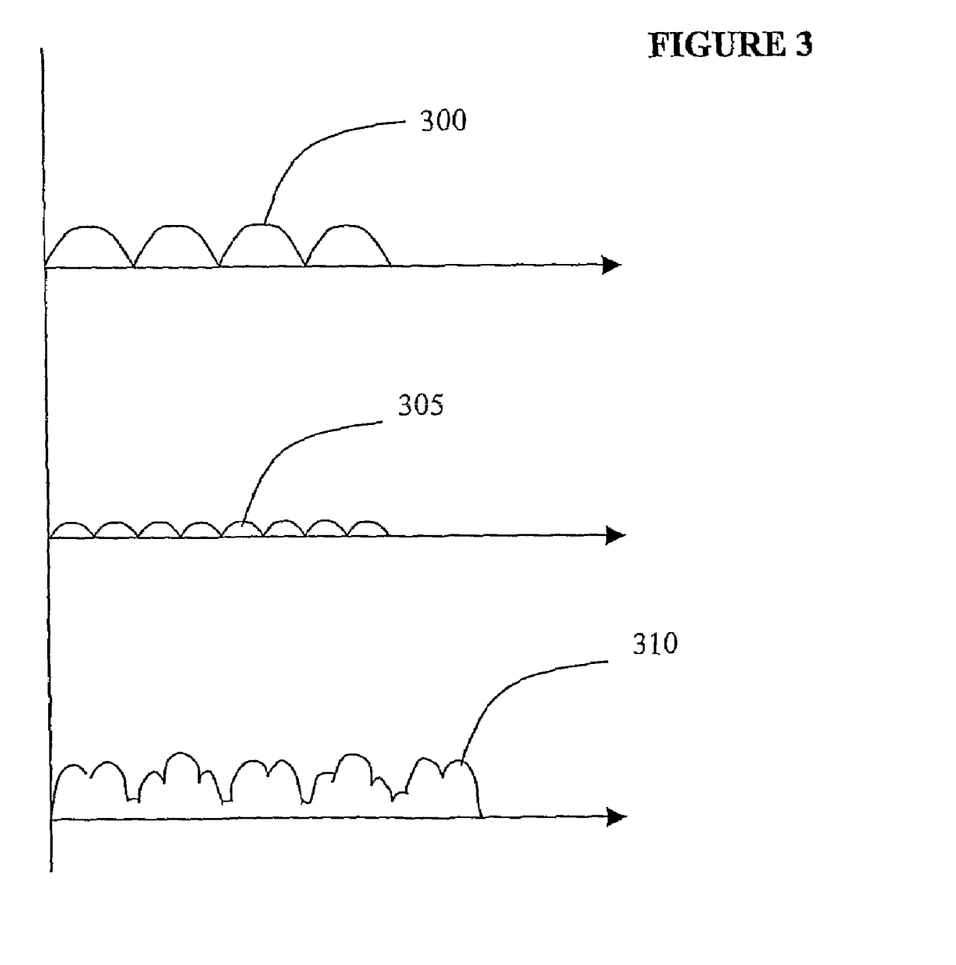
FIG. 3 shows two different sinusoidal modulation regimes and a possible detected output that might be present in use of the monitor of FIG. 1.

Referring to FIG. 3, an example might be for instance that the drive current controller produces a first drive current signal 300 to a first source 145 which is modulated at 5 kHZ and a second drive current signal 305 to a second source 160 which is modulated at 12 kHZ. These may then independently produce modulated fluorescence in a sample which in turn produces a modulated electrical output signal 310 at the detector 150. The electrical output signal 310 will show a more complex modulation which contains the frequencies of both regimes, that is 5 kHZ and 12 kHZ, superimposed. The presence or absence of either one of the modulation regimes in the detector's electrical output signal 310 will show the presence or absence of responses by probes to the two different sources 145, 160 and thus the presence or absence of relevant process activities in the sample.

Referring additionally to FIG. 1, in order to detect the respective modulation regimes in the electrical output 310 of the detector 150 in a relatively simple manner, the detector output 310 is delivered to a signal analyser 185 of known type, providing synchronous detection. The signal analyser 185 also receives the first and second drive current signals at 5 kHZ and 12 kHZ from the modulation arrangement 180. These drive current signals together with an oscilloscope can be used to tune the signal analyser 185 to sample the detector output 310 at the frequencies of the two modulation regimes it needs to detect in order to identify a separate fluorescent response to each of the sources 145, 160.

Figure 4:
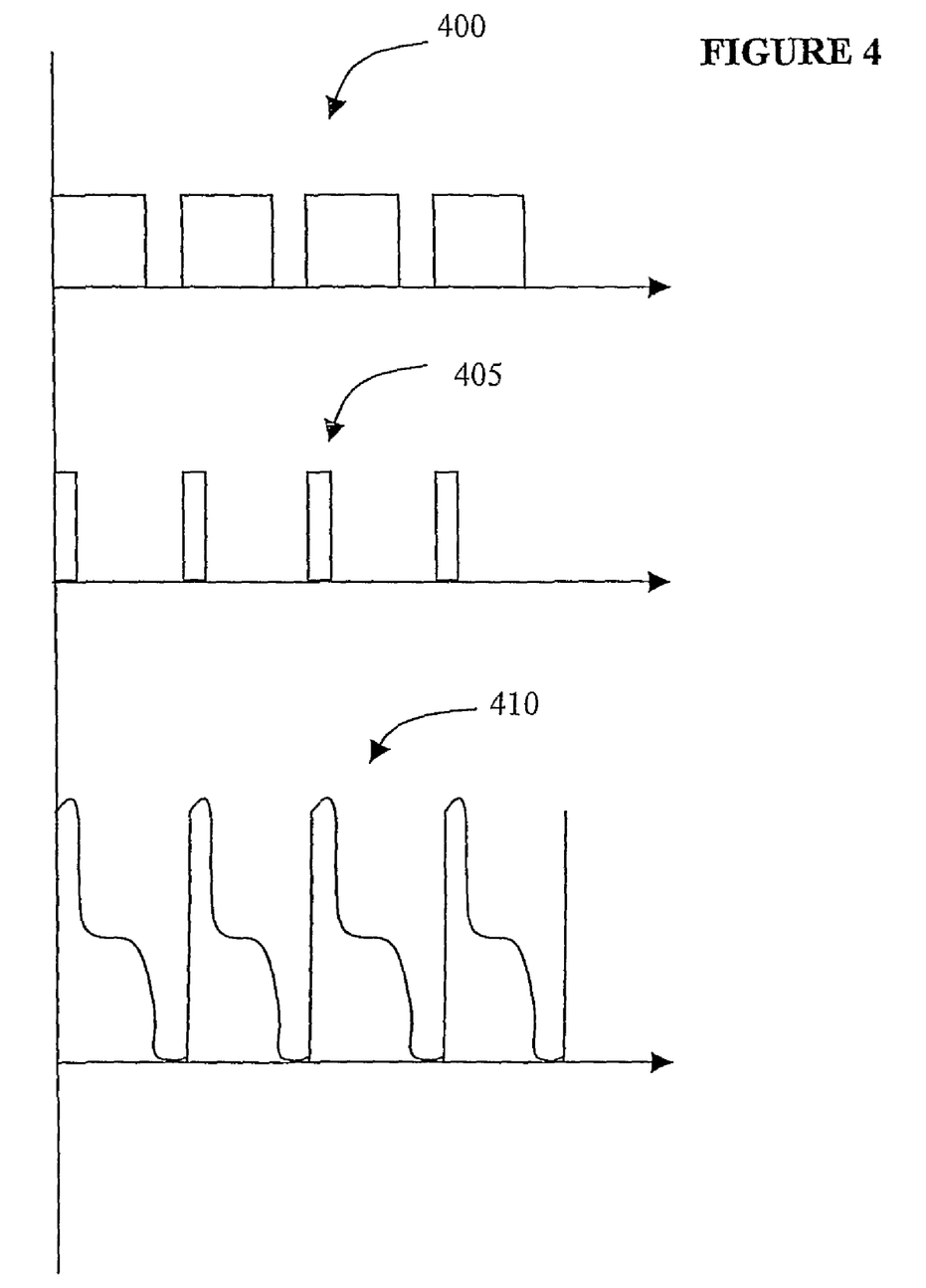
FIG. 4 shows two different pulse width modulation regimes and a possible detected output that might be present in use of the monitor of FIG. 1.

Referring to FIG. 4, as mentioned above, in an alternative form of modulation for use with synchronous detection, the modulation might instead take the form of pulse-based modulation, such as pulse width or repetition rate. In the example shown in FIG. 4, a first modulation regime is represented by a pulse train 400 having a duty ratio of 4:5 and a second modulation regime by a pulse train 405 having a duty ratio of 1:5. The fluorescent response of the sample 410 seen at the signal analyser 185 can then show components stemming from each of the modulation regimes which again can be separated by known detection techniques.

As mentioned above, the lifetime of fluorescence emission is of the order of 100 nanoseconds. The maximum practical modulation frequency, or pulse repetition rate, would therefore be around 10 MHz. The minimum would usually be set above mains frequency (50 Hz in Great Britain and 60 Hz in the US) in order to reduce a potential source of noise in the system. Appropriate pulse widths, or modulation in the pulse width, would lie in the range from 0.1 microseconds to approximately 10 milliseconds, this producing a modulation which is detectable in the frequency domain in the range from approximately 100 Hz to 10 MHz.

As shown in FIG. 4, pulse width is modulated but the pulse repetition rate remains the same between modulation regimes. Alternatively or additionally, a modulation regime might be applied by altering the pulse repetition rate.

Figure 5A:
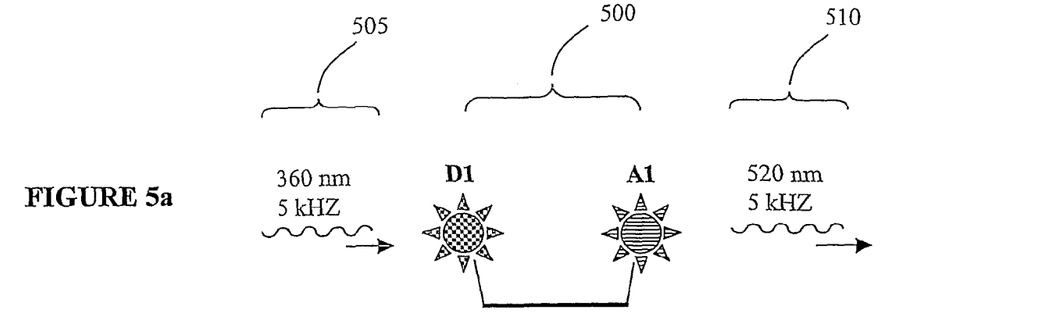
FIGS. 5, 6 and 7 show schematically three pairs of distinguishable probes for use in an assay using the monitor of FIG. 1.
Figure 5B:
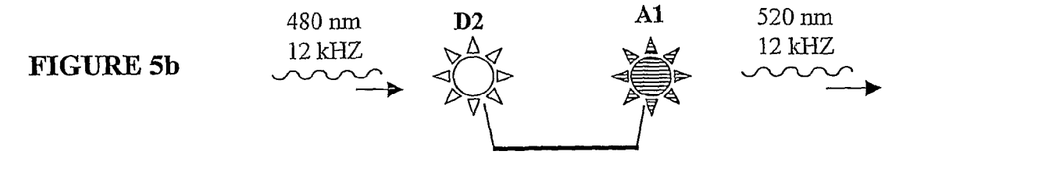
Figure 6A:
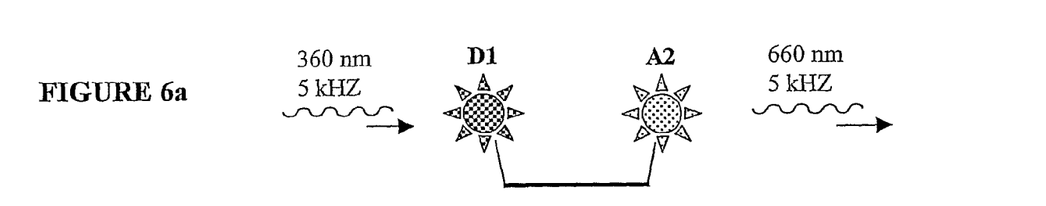
Figure 6B:
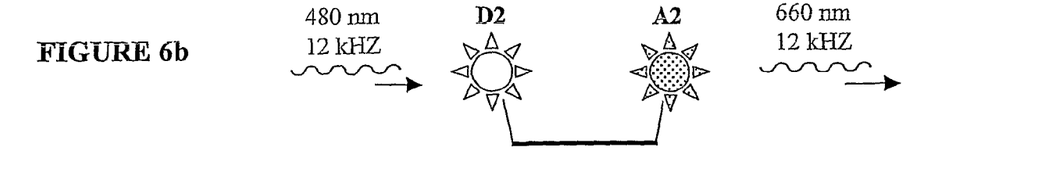
Figure 7A:
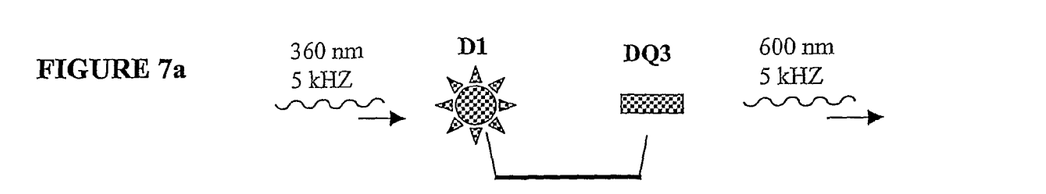
Figure 7B:
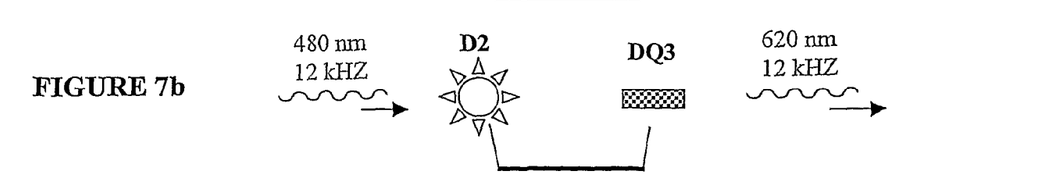

Referring to FIGS. 5 to 7, responses of various pairs of probes 500 together in the same sample and that have the same wavelength are indicated. Each pair of probes 500 is responding to modulated excitation radiation 505 and consequently produces modulated responses 510.

In each case, two sources 145, 160 are being used, one violet (360 nm) modulated at 5 kHZ and the other blue (480 nm) modulated at 12 kHZ. Referring to FIGS. 5 and 6, a first pair of probes 500 might both respond with modulated fluorescence 510 at 520 nm and a second pair of probes 500 might both respond with modulated fluorescence 510 at 660 nm. These pairs of probes 500 cannot be distinguished by wavelength but can be distinguished by their respective modulations since these will be "labelled" by the two modulation regimes of the drive currents to the sources: 5 kHZ and 12 kHZ.

Referring to FIG. 7, in a variation on the above, a pair of probes 500 may both use a dark quencher DQ3. In this case the reporters will be the respective donors D1, D2, giving fluorescence for instance at 600 nm and 620 mm. These wavelengths may be too close together to be clearly distinguished but again the detected fluorescence 510 carries the modulation regimes of the drive currents to the sources, 5 kHZ and 12 kHZ, and can thus be distinguished.

Figure 8:
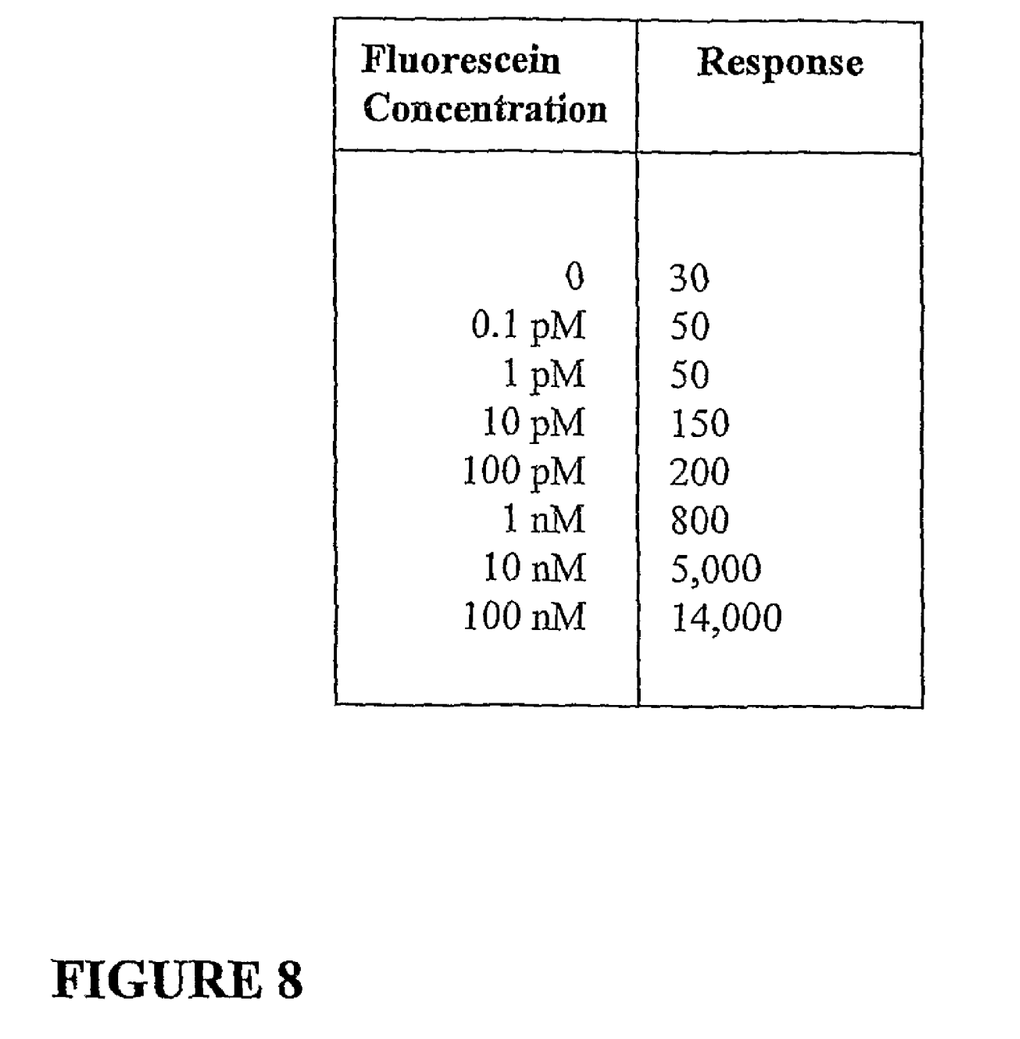
FIG. 8 shows limits of detection achievable by use of the monitor of FIG. 1.

Referring to FIG. 8, the sensitivity of embodiments of the present invention has been found to be very high compared with known, unmodulated apparatus. Using a series of solutions at different concentrations of a dye commonly used in probes, fluorescein, a voltage measured at the detector output with respect to modulated fluorescence began to show a clear signal above noise at a concentration of 10 pM fluorescein. At higher concentrations, the signal level increased significantly, being several times greater than that achieved with known arrangements for detecting the same fluorescence.

In the above description, separation of fluorescent responses by a sample to more than one different source can be done using simultaneous irradiation of the sample with all of the sources, the sources and respective responses thereto being "labelled" by the use of distinctive modulation regimes. It is already known to identify responses to different sources by wavelength. Different reporters may fluoresce at different wavelengths and it is known to use a filter at the detector 150 to limit detection to one reporter at a time. Alternatively, more sophisticated detection can be done, for example using a spectrofluorimeter or a fluorimeter with more than one optical detector. Examples of suitable systems are: Applied Biosystems 7700; Applied Biosystems 7000; the Roche LightCycler; the Cepheid SmartCycler; and the Corbett Rotor-Gene. By using modulation as well as wavelength discrimination in an embodiment of the present invention, it becomes possible to discriminate a much greater number of fluorescent responses. Hence where it has only been possible to discriminate up to four responses using wavelength discrimination alone in FRET-based assays, because of the wavelength characteristics of the fluorescent responses, using simple modulation regimes at the same time allows the number of responses discriminated to reach sixteen or potentially even more. This is based on using four modulation regimes and four sources of different wavelength. Light emitting diodes are already easily available to provide suitable sources.

Another advantage is the fact that the modulation regimes can be discriminated simultaneously. In known systems, it is often necessary to carry out sequential detection to detect the various wavelengths of the fluorescent responses. Thus the use of modulation regimes can allow the sample quantities to be reduced and overall assay times to be minimised.

In embodiments of the present invention, because there is no necessity for fluorescent responses to be at different wavelengths to be distinguished from one another, the filter in front of the detector 150 can be a simple long pass filter. Such a simplified optical arrangement, compared with known arrangements involving emission filters, might be found particularly useful in other types of assay arrangement, such as where the capillary tube 105 is replaced by a multi-well plate format.

The invention claimed is:

1. Apparatus for use in fluorescent resonant energy transfer assays for detecting the emission of fluorescent radiation from a sample in response to excitation by a radiation source, the sample containing at least two different probes, each probe comprising a donor/acceptor pair, the apparatus comprising:
   i) a sample irradiator for irradiating the sample with excitation radiation from at least two sources over the same time period, the two sources providing excitation radiation of different wavelengths;
   ii) a modulation arrangement for modulating the excitation radiation of each of said at least two sources according to a different respective modulation regime; and
   iii) an emission detector for detecting emission of fluorescent radiation from the sample, wherein the wavelength of the excitation radiation of each of said at least two sources is selected to excite a response from a different respective probe in the sample, and the emission detector is adapted to detect each of said different respective modulation regimes in emitted radiation such that responses of the at least two different probes to said at least two sources can be separately detected.

2. Apparatus according to claim 1 wherein the emission detector is adapted to detect emission of fluorescent radiation at a first wavelength and emission of fluorescent radiation at a second wavelength, whereby at least four different responses of the at least two different probes can be separately detected, distinguished in each case by modulation regime and/or by wavelength.

3. Apparatus according to claim 2 wherein said at least four different responses comprise responses of at least four different probes in the sample.

4. Apparatus according to claim 2 wherein the sample irradiator is adapted to irradiate the sample with excitation radiation from more than two sources over the same time period, the modulation arrangement being adapted to modulate the excitation radiation of each of said sources according to a different respective modulation regime, whereby at least six different responses of the at least two different probes can be separately detected, distinguished in each case by modulation regime and/or by wavelength.

5. Apparatus according to claim 1 wherein the sample irradiator comprises at least one radiation deflector for, in use, deflecting excitation radiation provided by at least one of said sources onto a path shared with excitation radiation provided by at least one other of said sources for delivery to the sample.

6. Apparatus according to claim 1 wherein the emission detector comprises a filter for filtering emission of fluorescent radiation from the sample, radiation showing at least two of said different respective modulation regimes being detected, in use of the apparatus, over the same time period via said filter.

7. Apparatus according to claim 1 wherein the modulation arrangement is adapted to modulate the intensity of the excitation radiation of at least one said source to give the modulation regime for that source.

8. Apparatus according to claim 1 wherein the excitation radiation emitted by at least one said source comprises a pulse train, the modulation arrangement being adapted to modulate the pulse train to give the modulation regime for that source.

9. Apparatus according to claim 8 wherein the modulation arrangement is adapted to modulate pulse width in the pulse train to give the modulation regime.

10. Apparatus according to claim 8 wherein the modulation arrangement is adapted to modulate pulse repetition rate in the pulse train to give the modulation regime.

11. Apparatus according to claim 1 wherein the modulation arrangement provides modulation detectable as a frequency in the frequency range from 65 Hz to 10 MHz.

12. Apparatus according to claim 1 wherein the sample comprises a biological sample.

13. Apparatus according to claim 1 wherein a process giving rise to detected emission of fluorescent radiation from the sample comprises a nucleic acid amplification reaction.

14. Apparatus according to claim 1 wherein a process giving rise to detected emission of fluorescent radiation from the sample comprises an immunoassay.

15. Apparatus according to claim 1 wherein a process giving rise to detected emission of fluorescent radiation from the sample comprises a nucleic acid hybridisation reaction.

16. Apparatus according to claim 1 wherein a process giving rise to detected emission of fluorescent radiation from the sample comprises a real-time polymerase chain reaction.

17. Apparatus for monitoring fluorescent radiation emitted from a sample during the course of a nucleic acid amplification reaction, in response to excitation by a radiation source, the apparatus comprising:
   i) a sample irradiator for irradiating the sample with excitation radiation from a source;
   ii) a modulation arrangement for modulating the excitation radiation according to a detectable modulation regime; and
   iii) an emission detector for detecting emission of fluorescent radiation from the sample, wherein the emission detector is adapted to detect said modulation regime in emitted radiation such that a response of the sample to the source can be detected in the presence of one or more other radiation inputs to the emission detector, said response being generated by a reporter system comprising donor/acceptor pairs in a process using fluorescent resonant energy transfer.

18. Apparatus according to claim 17 wherein the sample irradiator is adapted to irradiate the sample with excitation radiation from at least two different sources and the emission detector is adapted to detect two or more different responses of the sample, each response being generated by a different probe of the reporter system, each probe comprising a donor/acceptor pair.

19. Apparatus according to claim 17 wherein the modulation arrangement is adapted to modulate the intensity of the excitation radiation of at least one said source to give the modulation regime for that source.

20. Apparatus according to claim 17 wherein the excitation radiation emitted by at least one said source comprises a pulse train, the modulation arrangement being adapted to modulate the pulse train to give the modulation regime for that source.

21. Apparatus according to claim 20 wherein the modulation arrangement is adapted to modulate pulse width in the pulse train to give the modulation regime.

22. Apparatus according to claim 20 wherein the modulation arrangement is adapted to modulate pulse repetition rate in the pulse train to give the modulation regime.

23. Apparatus according to claim 17 wherein the modulation arrangement provides modulation detectable as a frequency in the frequency range from 65 Hz to 10 MHz.

24. Apparatus according to claim 17 wherein the sample comprises a biological sample.

25. Apparatus according to claim 17 wherein a process giving rise to detected emission of fluorescent radiation from the sample comprises a nucleic acid amplification reaction.

26. Apparatus according to claim 17 wherein a process giving rise to detected emission of fluorescent radiation from the sample comprises an immunoassay.

27. Apparatus according to claim 17 wherein a process giving rise to detected emission of fluorescent radiation from the sample comprises a nucleic acid hybridisation reaction.

28. APPARATUS according to claim 17 wherein a process giving rise to detected emission of fluorescent radiation from the sample comprises a real-time polymerase chain reaction.

29. A method of detecting fluorescent emissions from a sample containing at least two different fluorescent resonant energy transfer probes, each probe comprising a donor/acceptor pair, the method comprising the steps of:
  i) exciting the sample with excitation radiation from at least two sources over the same time period, the wavelength of the excitation radiation of each of said at least two sources being selected to excite a response from a different respective probe in the sample;
  ii) modulating the excitation radiation of each of said at least two sources according to a different respective modulation regime; and
  iii) detecting each of said different respective modulation regimes in emitted radiation such that responses of the at least two different probes to said at least two sources can be separately detected.

* * * * *

UNITED STATES PATENT AND TRADEMARK OFFICE
CERTIFICATE OF CORRECTION

| | | |
|---|---|---|
| PATENT NO. | : 7,652,266 B2 | |
| APPLICATION NO. | : 12/095444 | |
| DATED | : January 26, 2010 | |
| INVENTOR(S) | : David James Squirrell et al. | |

It is certified that error appears in the above-identified patent and that said Letters Patent is hereby corrected as shown below:

Claim 28, line 1: "APPARATUS" should read --Apparatus--

Signed and Sealed this
Twelfth Day of June, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,652,266 B2 | Page 1 of 1 |
| APPLICATION NO. | : 12/095444 | |
| DATED | : January 26, 2010 | |
| INVENTOR(S) | : David James Squirrell et al. | |

It is certified that error appears in the above-identified patent and that said Letters Patent is hereby corrected as shown below:

Column 13, line 18 (Claim 28, line 1) "APPARATUS" should read --Apparatus--

This certificate supersedes the Certificate of Correction issued June 12, 2012.

Signed and Sealed this
Third Day of July, 2012

David J. Kappos
*Director of the United States Patent and Trademark Office*